United States Patent [19]

Obong

[11] Patent Number: 5,733,261
[45] Date of Patent: Mar. 31, 1998

[54] SINGLE USE LOCKING SYRINGE

[76] Inventor: Ekoi Edet Obong, 645 Parsons St., SW. Atlanta, Ga. 30314

[21] Appl. No.: 613,491

[22] Filed: Mar. 8, 1996

[51] Int. Cl.⁶ .................................................. A61M 5/50
[52] U.S. Cl. ................................. 604/110; 604/210
[58] Field of Search .......................... 604/110, 218, 604/220, 210, 228, 187

[56] References Cited

U.S. PATENT DOCUMENTS

| | | | |
|---|---|---|---|
| 2,875,761 | 3/1959 | Helmer et al. | 604/210 |
| 3,938,505 | 2/1976 | Jamshidi | 604/210 X |
| 4,642,102 | 2/1987 | Ohmori | 604/210 |
| 4,978,339 | 12/1990 | Lobouze et al. | 604/110 |
| 5,114,405 | 5/1992 | Winter | 604/110 |
| 5,181,909 | 1/1993 | McFarlane | 604/52 |
| 5,215,524 | 6/1993 | Vallelunga et al. | 604/110 |
| 5,259,890 | 11/1993 | Boris | 604/110 |
| 5,263,934 | 11/1993 | Haak | 604/110 |
| 5,429,610 | 7/1995 | Vailancourt | 604/191 |
| 5,468,232 | 11/1995 | Naganuma | 604/200 |

Primary Examiner—Michael Powell Buiz
Assistant Examiner—A. T. Nguyen
Attorney, Agent, or Firm—Herbert M. Hanegan; J. Rodgers Lunsford, III

[57] ABSTRACT

A locking syringe is disclosed which comprises a plunger, a cylinder, and a locking member for preventing the syringe to be used more than one time. The plunger includes an indention near its upper end into which a plunger locking member fits when the plunger is pushed and approaches the lower end of the cylinder to administer injections or remove bodily fluids and prevents re-use of the syringe by preventing removal of the plunger from the cylinder after the syringe has been used. The cylinder comprises an open cylindrical passage and includes a needle attached in a conventional manner at the end thereof.

11 Claims, 1 Drawing Sheet

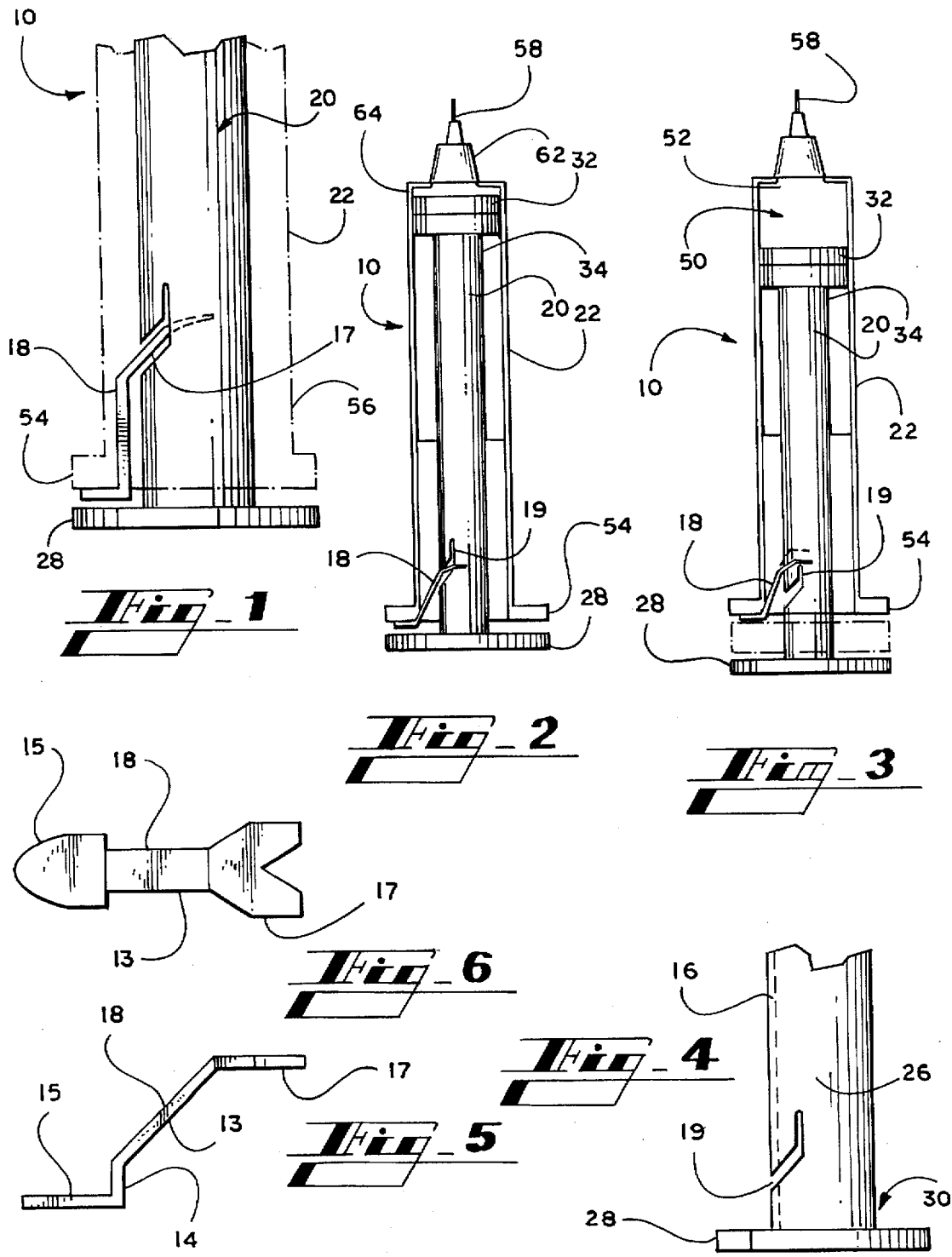

SINGLE USE LOCKING SYRINGE

FIELD OF THE INVENTION

The invention relates to hypodermic syringes, and, in particular, to a syringe which can only be used once and which can be disposed of safely.

BACKGROUND OF THE INVENTION

Many serious and communicable diseases can be transmitted through the blood of an infected person. It is well known that viruses and bacteria are often carried in blood and can be passed on to others through contact with the contaminated blood. One such disease which can be spread by contact with a sample of blood carrying the virus is AIDS, for which there is currently no cure. This disease has spread to significant proportions due to transmission of the virus through blood or other bodily fluids of infected persons.

Medical personnel are particularly susceptible to the spread of disease because of their frequent contact with the carriers of the disease. Syringes used to administer injections or remove bodily fluids for testing pose a substantial risk to doctors, nurses, and other medical personnel because of the chance of contact with the blood or bodily fluid and the possibility that the disease may enter the bloodstream of the medical technician through an exposed cut or abrasion or an accidental needle prick. For this reason, it is desirable that hypodermic syringes used to administer injections or extract bodily fluids for analysis and testing comprise a safety system that prevents their re-use.

The spread of highly communicable diseases such as AIDS can be effected by re-use of the hypodermic needles and syringes. The needles are often sought by drug addicts to inject drugs intravenously into the blood stream. When used by drug addicts, the needles are often unclean and unsterilized, and thus, any virus or bacteria contained within residual blood or body fluids from the previous user is readily transmitted to the drug addict. The needles are often shared by the drug users, resulting in further spread of any bacteria or viruses contained in bodily fluids carried on the needles. Therefore, it is desirable to design a syringe such that it can not be re-used.

Several syringes have been provided with protective elements in an attempt to prevent re-use of the needle. One such syringe is described in U.S. Pat. No. 4,820,272. The syringe comprises a cylinder having a series of inwardly extending grooves formed near the top end and a plunger having a mating series of outwardly extending grooves formed at the bottom end. These grooves allow the full insertion of the plunger within the cylinder but impede its withdrawal. French patent publication 2613628 discloses a similar type of syringe having flexible teeth formed in a piston which engage teeth in an outer tubular body to allow movement of the piston in one direction only. U.S. Pat. No. 4,731,068 also discloses a syringe including means to prohibit retraction of the plunger once the contents of the syringe have been discharged. Other types of non-reusable syringes are disclosed in U.S. Pat. Nos. 5,114,405 and 5,259,840.

SUMMARY OF THE INVENTION

The present invention provides a syringe which ensures that the syringe cannot be used more than one time. The syringe includes a locking member which cooperates with a plunger which slides within an open, cylindrical passage in a cylinder. A needle is positioned at the end of the cylinder and discharges liquid through an opening as the plunger forces the liquid to the bottom of the cylinder.

In this invention the sharing of syringes with needles is avoided by a syringe design which makes it virtually impossible to employ a syringe after one use and is also difficult to tamper with.

By prohibiting re-use and accidental needle contact, the syringe further provides assurance and security to persons receiving injections.

A preferred embodiment of this invention consists of a syringe having a plunger and a locking member engagable therewith which prevents the plunger from being retracted after use and is designed to inhibit the avoidance of the locking device.

It is thus a principal object of this invention to provide a syringe which is incapable of more than a single use.

Other objects and advantages of this invention will hereinafter become obvious from the following detailed description of a preferred embodiment of this invention.

BRIEF DESCRIPTION OF THE DRAWINGS

FIG. 1 is a cross-sectional view of a locking syringe in accordance with the present invention showing the plunger and locking means;

FIG. 2 is a side cross-sectional view of the plunger with the locking means engaged;

FIG. 3 is a cross-sectional view of the plunger with the locking means not engaged;

FIG. 4 is a side view of the plunger;

FIG. 5 is a side view of the plunger locking member;

FIG. 6 is a top view of the plunger locking member.

DESCRIPTION OF THE PREFERRED EMBODIMENTS

Referring to the Figures wherein like features are numbered identically throughout, the locking syringe 10 of the present invention comprises a plunger 20 and a housing or cylinder 22. The plunger 20 is preferably a standard syringe plunger formed of polystyrene or polypropylene and comprises a shaft 26 having a cross-section as best illustrated in FIG. 4. The plunger 20 is preferably formed of medical grade LEXAN polycarbonate polymer having a 10% glass fill and includes a circular grip or thrust plate 28 located at the upper end 30 of the shaft 26. Optionally, a piston 32 is attached in a known manner to a proximal end 34 of the shaft 26, opposite the thrust plate 28. As best shown in FIG. 4, the thrust plate 28 is advantageously molded to end 30 of the shaft 26 or formed as a single element with shaft 26 to comprise the plunger 20. Plunger 20 has an indention 19, near the top end of shaft 26 which plunger locking member 18 comprising a leaf spring having two spring ends connected by an intermediate spring portion, a first spring end being supported at the first open end of the tube end, a second spring end extending into said bore with said plunger, said second spring end being engagable in said angled slot when the plunger moves into the bore a given distance, preferably the second spring end is bifurcated engages and fits into when plunger 20 is at its lower most point of travel in cylinder 22, i.e., at the completion of an injection.

The cylinder 22 comprises an open, cylindrical passage 50 surrounded by an inner wall 52 and is also preferably formed of medical grade Lexan having a 10% glass fill. A grip or handle 54 is formed at an upper end 56 of the cylinder 22. A needle 58 is conventionally engaged to a neck portion 62 at a proximal end 64 of the cylinder 22. An optional syringe cap may also be formed of medical grade Lexan having a 10% glass fill and having a wide opening mouth sized to cover the proximal end 64 of the cylinder 22, and tapering in width, having sufficient length and width to enclose the needle 58.

The plunger locking member 18 prevents re-use of the syringe once an injection has been given. Preferably, the plunger locking member 18 engages and fits into indention 19 when an injection is completed, i.e., when shaft 26 approaches its lowest point in cylinder 22, the shaft indention 19 clears plunger locking member 18 which then fits into indention 19 preventing withdrawal of shaft 26, resisting rotation of shaft 26 in any attempt to tamper with or defeat the locking member, and prevents re-use of the syringe. Plunger locking member 18 advantageously is formed or shaped so that it applies a tension force against the plunger thereby springing into the indention 19 when plunger 20 has moved a given distance within cylinder 22 and preventing removal therefrom. Preferably the plunger locking member 18 is made of material compatible with the plunger and cylinder such as polystyrene, polypropylene, Lexan, aluminum, steel, and other metals, fibers polymers and mixtures thereof. It should be apparent to those skilled in the art, however, that other materials which create a snap, press, or other deformable locking fit could also be used.

Preferably plunger locking member 18 is formed with a void or a V-shaped end 17 which matingly contacts any spline 16 on shaft 26 thereby resisting rotation of shaft 26 in an effort to defeat the locking means.

In operation of the locking syringe the plunger 20 is inserted within the cylindrical passage 50 and is free to move within the cylinder 22, to back out to draw fluid into the cylinder 22 and to dispense fluid by pressing plunger 20 until it approaches its lowest point in cylinder 22 engaging plunger locking member 18.

By retracting the plunger 20 upwardly, liquid to be delivered by way of syringe 10 is drawn in through the needle 58 and any air present within the cylindrical passage 50 is expelled by inverting syringe 10 and pressing plunger 20 forwardly until the liquid begins to come out of the needle. After the desired amount of fluid has been drawn into the cylinder 22, the syringe is ready for the administration of an injection and the plunger 20 is again moved relative to the cylinder 22, using the thrust plate 28 and the handle 54. As the piston 32 carded on the plunger 20 travels the length of the passage 50, the liquid contained within the passage 50 is forced out through the needle 58.

When the liquid in the passage 50 has been ejected and the plunger 20 approaches its lowermost point within cylinder 22, plunger locking member 18 engages and snaps into indention 19 of the plunger 20. As described above, the plunger 20 and cylinder 22 are preferably formed of medical grade Lexan, however, plunger locking member 18 can be formed of these or other materials which permit a snap fit. As is well known, a snap fit of this type requires that the material be somewhat flexible to permit plunger locking member 18 to bend and then snap back into indention 19 to hold the plunger 20 once it has been completely inserted to the lowermost point within cylinder 22 to prevent motion of plunger 20 within cylinder 22, whereby the syringe cannot be used again.

Plunger locking member 18 fits within a standard syringe cylinder without any modification to the standard cylinder. Plunger 20 may be manufactured with indention 19 therein or such an indention may be cut or formed in plunger 20 prior to assembly of the syringe. Plunger locking member 18 is retained between plunger 20 and the walls of cylinder 22 prior to use by tension forces resulting from the shape and materials of manufacture of plunger locking member 18.

As can be best understood by viewing FIGS. 1–3 and 5, plunger locking member 18 must be flexible enough to be inserted within cylinder 22 of syringe 10 between shaft 26 and inner wall 52 of cylindrical passage 50. Plunger locking member 18 preferably is formed with one end having a notch or V-shape 17 and the other end 15 being substantially flat. As can be seen from FIG. 5, plunger locking member 18 in its untensioned state has a short length of shaft 14 connected to end 15 at approximately 90°. Flat surface end 15 has a length which may be greater than shaft 14 depending upon the size and type of syringe used, it being only necessary that the length of end 15 be sufficient to fit between thrust plate 28 and handle 54 so as to retain plunger locking member 18 within the syringe. As shown in FIG. 5, plunger locking member 18 has an elongated shaft 13 attached to short shaft 14 preferably at an angle of from greater than about 90° to less than about 180°. End 17 of plunger locking member 18 is attached to the opposite end of elongated shaft 13 preferably forming an angle of attachment with shaft 13 of from greater than about 90° to less than about 180°.

Thus, it can be seen that upon insertion between shaft 26 and inner wall 52, plunger locking member 18 by virtue of the degree of angles formed between short shaft 14 and elongated shaft 13, and between elongated shaft 13 and end 17, forms a spring and exerts a tension force which retains plunger locking member 18 within the syringe, and which upon administering an injection forces plunger locking member 18 into indention 19. Where shaft 26 contains splines 16, plunger locking member 18 prevents the turning or twisting of shaft 26 since end 17 engages such splines, thereby preventing the disabling of the locking means.

What is claimed is:

1. A locking syringe comprising:

a tube having a bore, a first open end and a second end;

means at said second end for connecting a needle to said tube;

a plunger movable into said first open end and said bore, said plunger having an indention therein;

a plunger locking member extending into said bore and being engagable in said indention when said plunger moves into said bore a given distance thereby preventing removal of said plunger from said bore, said plunger locking member comprising a spring element extending into said bore, said spring element being biased toward and engagable in tension against said plunger, the bias in said spring element urging said element into said indention when said plunger moves into said bore said given distance, said indention comprising an angled slot in said plunger and said spring element comprising a leaf spring having two spring ends connected by an intermediate spring portion, a first spring end being supported at the first open end of the tube and a second spring end extending into said bore with said plunger, said second spring end being engagable in said angled slot when said plunger moves into said bore said given distance.

2. The locking syringe of claim 1, wherein said intermediate portion of said leaf spring element includes at least one bend so as to bias said spring element toward said plunger.

3. The locking syringe of claim 1, wherein said second spring end is bifurcated.

4. The locking syringe of claim 1, wherein the tube and plunger are manufactured of a material selected from the group consisting of polymers, fibers, and mixtures thereof.

5. The locking syringe of claim 4 manufactured of polystyrene.

6. The locking syringe of claim 4 manufactured of polypropylene.

7. The locking syringe of claim 4 manufactured of a polycarbonate polymer.

8. The locking syringe of claim 1 wherein the plunger locking member is manufactured of a material selected from the group consisting of polymers, metals, fibers, and mixtures thereof.

9. The locking syringe of claim 1, wherein the plunger locking member applies a continuous tension force upon insertion between the plunger and a wall of the bore.

10. A locking syringe comprising:
   a syringe body having:
      a distal end,
      a proximal end,
      an open cylindrical passage,
      a plunger for slidable insertion in said cylindrical passage, said plunger having an indention therein,
      the distal end adapted to hold a needle, said cylindrical passage being otherwise free of locking members;
   the plunger comprising a shaft having a proximal end and a distal end, said indention located on the proximal end of said shaft, said plunger locking member being engagable in said indention when said plunger approaches the lowermost point in said cylindrical passage, thereby prohibiting removal of said plunger from said cylindrical passage, said plunger being otherwise free of locking members, said plunger locking member comprising a spring element extending into said cylindrical passage, said spring element being biased toward and engagable in tension against said plunger, the bias in said spring element urging said element into said indention when said plunger moves into said cylindrical passage said given distance, said indention comprising an angled slot in said plunger, and said spring element comprising a leaf spring having two spring ends connected by an intermediate spring portion, a first spring end being supported at the proximal end of the body and a second spring end extending into said cylindrical passage with said plunger, said second spring end being engagable in said angled slot when said plunger moves into said cylindrical passage said given distance.

11. A method for administering an injection of a fluid using a syringe, said method comprising the steps of:
   providing a syringe plunger having an indention located only at its proximal end;
   providing a syringe body having proximal and distal ends, a cylindrical passage, with a locking element located only adjacent the proximal end of said cylindrical passage;
   depressing said plunger into said cylindrical passage of said syringe body, thereby moving said plunger from the proximal end and approaching the distal end of said cylindrical passage thereby injecting the fluid and engaging said locking element in the indention on said plunger to prevent removal of said plunger from said cylindrical passage, said plunger locking member comprising a spring element extending into said cylindrical passage, said spring element being biased toward and engagable in tension against said plunger, the bias in said spring element urging said element into said indention when said plunger moves into said cylindrical passage a given distance, said indention comprising an angled slot in said plunger, and said spring element comprises a leaf spring having two spring ends connected by an intermediate spring portion, a first spring end being supported at a first open end of the cylindrical passage and a second spring end extending into said cylindrical passage with said plunger, said second spring end being engagable in said angled slot when said plunger moves into said cylindrical passage said given distance.

* * * * *